United States Patent
Kapadia et al.

(10) Patent No.: US 12,059,220 B2
(45) Date of Patent: Aug. 13, 2024

(54) ROBOTIC SURGICAL SYSTEMS AND ROBOTIC ARM CARTS THEREOF

(71) Applicant: Covidien LP, Mansfield, MA (US)

(72) Inventors: Jaimeen Kapadia, Cambridge, MA (US); Shane Reardon, Branford, CT (US)

(73) Assignee: Covidien LP, Mansfield, MA (US)

( * ) Notice: Subject to any disclaimer, the term of this patent is extended or adjusted under 35 U.S.C. 154(b) by 504 days.

(21) Appl. No.: 17/434,864

(22) PCT Filed: Mar. 5, 2020

(86) PCT No.: PCT/US2020/021254
§ 371 (c)(1),
(2) Date: Aug. 30, 2021

(87) PCT Pub. No.: WO2020/185524
PCT Pub. Date: Sep. 17, 2020

(65) Prior Publication Data
US 2022/0151713 A1 May 19, 2022

Related U.S. Application Data

(60) Provisional application No. 62/818,152, filed on Mar. 14, 2019.

(51) Int. Cl.
*A61B 50/13* (2016.01)
*A61B 17/00* (2006.01)
(Continued)

(52) U.S. Cl.
CPC .............. *A61B 34/30* (2016.02); *A61B 17/00* (2013.01); *A61B 50/13* (2016.02); *A61B 90/50* (2016.02);
(Continued)

(58) Field of Classification Search
CPC ......... A61B 34/30; A61B 17/00; A61B 50/13; A61B 90/50; A61B 2017/00477;
(Continued)

(56) References Cited

U.S. PATENT DOCUMENTS 5,579,871 A * 12/1996 Emmrich .............. B60B 33/026
188/19
8,828,023 B2   9/2014 Neff et al.
(Continued)

FOREIGN PATENT DOCUMENTS

CN      204895531 U  * 12/2015
CN      204895531 U    12/2015
(Continued)

OTHER PUBLICATIONS

International Search Report issued in corresponding to International Appln. No. PCT/US2020/021254 dated Jun. 30, 2020, 2 pages.
(Continued)

*Primary Examiner* — James A Shriver, II
*Assistant Examiner* — Ian Bryce Shelton
(74) *Attorney, Agent, or Firm* — Carter, DeLuca & Farrell LLP

(57) ABSTRACT

A surgical cart for supporting a robotic arm includes a base, a plurality of casters coupled to the base, and first and second rods rotatably supported by the base. The first rod is operably coupled to a first caster and configured to rotate in a first direction to one of lock or unlock the first caster. The second rod is coupled to a second caster and operably coupled to the first rod such that rotation of the first rod in the first direction causes the second rod to rotate in a second direction to one of lock or unlock the second caster.

20 Claims, 6 Drawing Sheets

(51) Int. Cl.
*A61B 34/30* (2016.01)
*A61B 90/50* (2016.01)

(52) U.S. Cl.
CPC .............. *A61B 2017/00477* (2013.01); *A61B 2090/508* (2016.02)

(58) Field of Classification Search
CPC ........ A61B 2090/508; A61B 2034/302; B60B 33/0092; B60B 33/021; B60B 33/026; B60B 33/02; B62B 5/04; B62B 5/0433; B62B 5/0457; B62B 9/08; B62B 9/082; B62B 9/087
See application file for complete search history.

(56) References Cited

U.S. PATENT DOCUMENTS

| | | | |
|---|---|---|---|
| 10,667,772 B2 * | 6/2020 | Mikami | A61B 6/4405 |
| 11,357,583 B2 * | 6/2022 | Li | A61B 1/00128 |
| 11,432,899 B2 * | 9/2022 | Hirose | A61B 90/37 |
| 2006/0082088 A1 | 4/2006 | Webster et al. | |
| 2007/0044272 A1 * | 3/2007 | Misin | B60B 33/0042 |
| | | | 16/35 R |
| 2010/0122430 A1 * | 5/2010 | Ahn | B60B 33/0073 |
| | | | 16/37 |
| 2012/0311821 A1 | 12/2012 | Eguchi | |
| 2013/0111664 A1 * | 5/2013 | Childs | B60B 33/026 |
| | | | 280/80.1 |
| 2013/0160237 A1 * | 6/2013 | Shih | B60B 33/025 |
| | | | 16/47 |
| 2013/0174377 A1 * | 7/2013 | Lin | B60B 33/0081 |
| | | | 16/35 R |
| 2017/0057284 A1 * | 3/2017 | Wang | B62B 3/001 |
| 2017/0065355 A1 * | 3/2017 | Ross | A61B 34/30 |
| 2017/0087730 A1 | 3/2017 | Robinson | |
| 2018/0199900 A1 * | 7/2018 | Mikami | A61B 6/4429 |
| 2019/0060005 A1 | 2/2019 | Iceman et al. | |
| 2019/0167377 A1 * | 6/2019 | Hirose | G02B 21/0012 |
| 2020/0046441 A1 * | 2/2020 | Liu | A61B 34/30 |
| 2020/0093564 A1 * | 3/2020 | Hirose | A61B 34/20 |
| 2021/0145527 A1 * | 5/2021 | Li | A61B 50/13 |

FOREIGN PATENT DOCUMENTS

| | | | | |
|---|---|---|---|---|
| CN | 108248659 A | * | 7/2018 | |
| CN | 108609044 A | * | 10/2018 | ........... B62B 5/0433 |
| CN | 108706036 A | * | 10/2018 | ........... A61G 7/0528 |
| CN | 108706036 A | | 10/2018 | |
| CN | 208021107 U | * | 10/2018 | ........ B60B 33/0078 |
| CN | 208021107 U | | 10/2018 | |
| KR | 20150037639 A | * | 4/2015 | |
| KR | 20170056719 A | * | 5/2017 | |
| WO | WO-2014198234 A1 | * | 12/2014 | ........... A61G 13/104 |
| WO | WO-2017028035 A1 | * | 2/2017 | .............. A61B 8/00 |
| WO | WO-2018055888 A1 | * | 3/2018 | ............. A61B 90/25 |
| WO | WO-2020000935 A1 | * | 1/2020 | ........... A61G 7/0528 |

OTHER PUBLICATIONS

Extended European Search Report issued in corresponding application EP 20769260.9 dated Nov. 16, 2022 (7 pages).

* cited by examiner

ROBOTIC SURGICAL SYSTEMS AND ROBOTIC ARM CARTS THEREOF

CROSS-REFERENCE TO RELATED APPLICATIONS

This application is a national stage entry of PCT/US2020/021254 filed on Mar. 5, 2020, which claims the benefit of and priority to U.S. Provisional Application No. 62/818,152 filed on Mar. 14, 2019, the entire contents of each of which are incorporated by reference herein.

FIELD OF THE INVENTION

The present invention relates to robotic surgical systems used in minimally invasive medical procedures because of their increased accuracy and expediency relative to handheld surgical instruments.

BACKGROUND

Robotic surgical systems are used in minimally invasive medical procedures because of their increased accuracy and expediency relative to handheld surgical instruments. In these robotic surgical systems, a robotic arm supports a surgical instrument having an end effector mounted thereto by a wrist assembly. In operation, the robotic arm is moved to a position over a patient and then guides the surgical instrument into a small incision via a surgical port or a natural orifice of a patient to position the end effector at a work site within the patient's body.

Some robotic surgical systems employ a cart to support the robotic arm and allow a clinician to move the robotic arm to different locations within the operating room. While performing a surgical procedure, it would be desirable for the cart to be held in a stationary position.

SUMMARY

In an aspect of the present disclosure, a surgical cart for supporting a robotic arm is provided and includes a base, a plurality of casters coupled to the base, a first rod rotatably supported by the base and operably coupled to a first caster of the plurality of casters, and a second rod rotatably supported by the base and operably coupled to a second caster. The first rod is configured to rotate in a first direction to one of lock or unlock the first caster, and the second rod is operably coupled to the first rod such that rotation of the first rod in the first direction causes the second rod to rotate in a second direction to one of lock or unlock the second caster.

In some aspects, rotation of the second rod in the first direction may be configured to cause the first rod to rotate in the second direction to the other of lock or unlock the first and second casters.

In further aspects, the first and second rods may be parallel to one another.

In other aspects, the surgical cart may further include a first pedal coupled to the first rod, and a second pedal coupled to the second rod. The first pedal may be configured to rotate the first rod in the first direction and in turn rotate the second rod in the second direction. The second pedal may be configured to rotate the second rod in the first direction and in turn rotate the first rod in the second direction.

In aspects, rotation of the first rod in the first direction may unlock the first caster and rotation of the second rod in the second direction may unlock the second caster. Rotation of the second rod in the first direction may lock the second caster and rotation of the first rod in the second direction may lock the first caster.

In some aspects, the surgical cart may further include a first linkage having a first end rotationally coupled to a first crank of the first rod, and a second end operably coupled to the first caster. Rotation of the first rod in the first direction may move the first linkage via the first crank to one of lock or unlock the first caster.

In further aspects, rotation of the first rod in the second direction may move the first linkage via the first crank to the other of lock or unlock the first caster.

In other aspects, the first linkage may be perpendicular to the first and second rods.

In aspects, the first caster may have a crank operably coupled thereto. The second end of the first linkage may be rotationally coupled to the crank of the first caster such that the movement of the first linkage rotates the crank of the first caster to one of lock or unlock the first caster.

In some aspects, the first caster may have a locking bar non-rotationally coupled to the crank of the first caster. Rotation of the locking bar via the crank of the first caster may one of lock or unlock the first caster.

In further aspects, the surgical cart may further include a second linkage having a first end rotationally coupled to a second crank of the first rod, and a second end operably coupled to a third caster of the plurality of casters. Rotation of the first rod in the first direction may move the second linkage via the second crank to one of lock or unlock the third caster.

In other aspects, the first and second linkages may be perpendicular to the first and second rods.

In aspects, the third caster may have a crank operably coupled thereto. The second end of the second linkage may be rotationally coupled to the crank of the third caster, such that the movement of the second linkage rotates the crank of the third caster to one of lock or unlock the third caster.

In some aspects, the third caster may have a locking bar non-rotationally coupled to the crank of the third caster, such that rotation of the locking bar of the third caster via the crank of the third caster one of locks or unlocks the third caster.

In further aspects, the surgical cart may further include a first arm having a first end rotationally coupled to a first crank of the second rod, and a second end operably coupled to the second caster. Rotation of the second rod in the second direction may move the first arm via the first crank of the second rod to one of lock or unlock the second caster.

In other aspects, rotation of the second rod in the first direction may move the first arm via the first crank of the second rod to the other of lock or unlock the second caster.

In aspects, the second caster may have a crank operably coupled thereto. The second end of the first arm may be rotationally coupled to the crank of the second caster, such that the movement of the first arm rotates the crank of the second caster to one of lock or unlock the second caster.

In some aspects, the surgical cart may further include a second arm having a first end rotationally coupled to a second crank of the second rod, and a second end operably coupled to a fourth caster of the plurality of casters. Rotation of the second rod in the first direction may move the second arm via the second crank of the second rod to one of lock or unlock the fourth caster.

In further aspects, each of the first and second rods may have a gear non-rotationally coupled thereto. The gears of the first and second rods interface with one another.

In other aspects, locking the first caster may include preventing rotation of a wheel of the first caster and/or preventing swiveling of the first caster.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
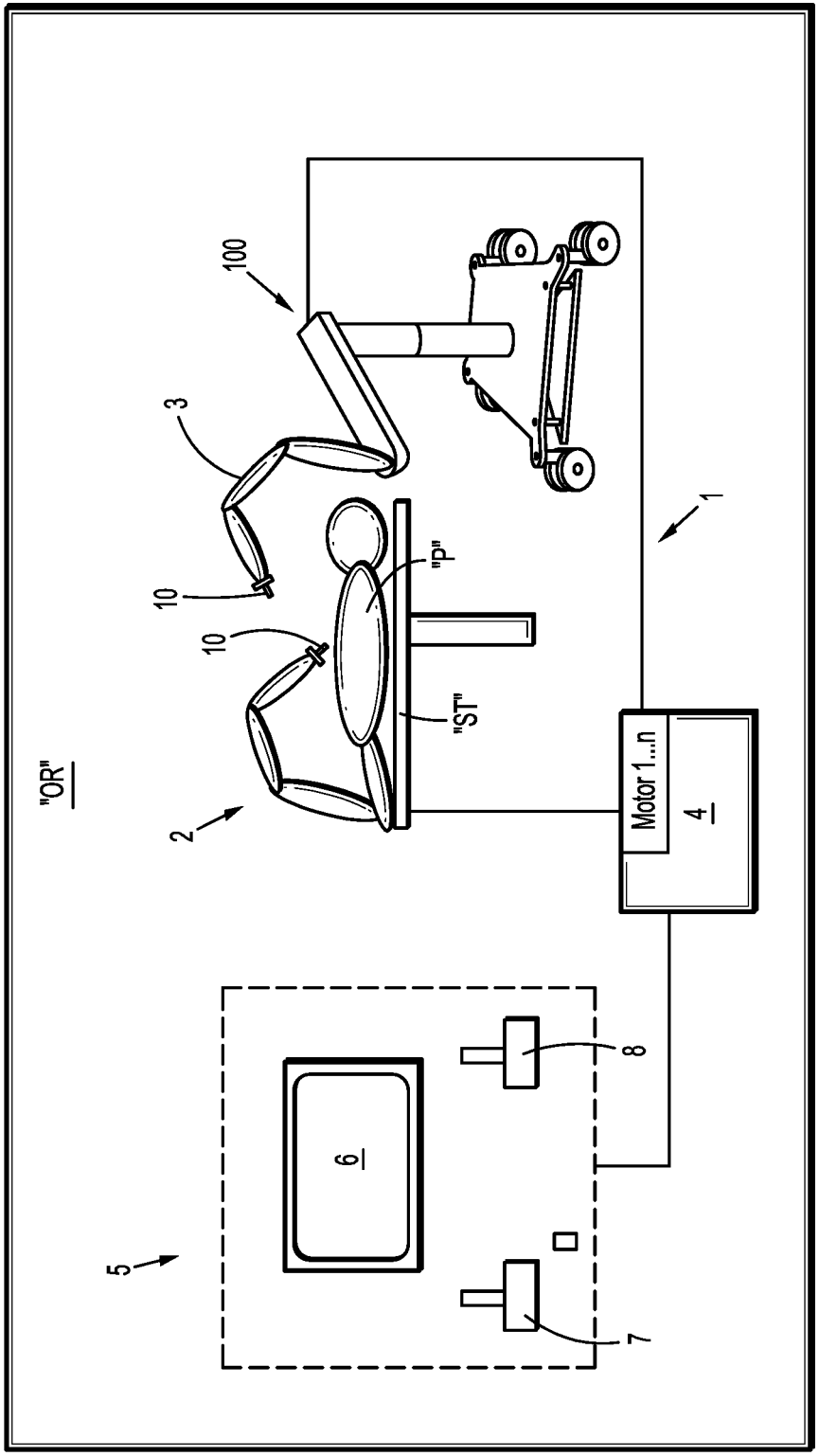
FIG. 1 is a schematic illustration of a robotic surgical system including a surgical cart in accordance with the present disclosure.

Embodiments of the presently disclosed robotic surgical systems including various embodiments of a robotic arm cart and methods of use thereof are described in detail with reference to the drawings, in which like reference numerals designate identical or corresponding elements in each of the several views. As used herein the term "distal" refers to that portion of the robotic surgical system or component thereof, that is closer to the patient, while the term "proximal" refers to that portion of the robotic surgical system or component thereof, that is farther from the patient.

As will be described in detail below, provided are embodiments of a surgical cart for supporting a robotic arm and for facilitating movement of the robotic arm around an operating room. The cart includes a base equipped with wheels, a support column extending vertically from the base, and a braking system that includes a series of interconnected linkages allowing for the selective locking and unlocking of the wheels of the cart.

Referring initially to FIG. 1, a surgical system, such as, for example, a robotic surgical system 1 is shown. In embodiments, robotic surgical system 1 is located in an operating room "OR." Robotic surgical system 1 generally includes a plurality of surgical robotic arms 2, 3 having a surgical instrument, such as, for example, an electromechanical instrument 10 removably attached thereto; a control device 4; and an operating console 5 coupled with control device 4.

Operating console 5 includes a display device 6, which is set up in particular to display three-dimensional images; and manual input devices 7, 8, by means of which a person (not shown), e.g., a clinician, is able to telemanipulate robotic arms 2, 3 in a first operating mode, as known in principle to a person skilled in the art. Each of the robotic arms 2, 3 may be composed of a plurality of members, which are connected through joints.

Robotic arms 2, 3 may be driven by electric drives (not shown) that are connected to control device 4. Control device 4 (e.g., a computer) is set up to activate the drives, in particular by means of a computer program, in such a way that robotic arms 2, 3 and thus electromechanical instrument 10 (including the electromechanical end effector (not shown)) execute a desired movement according to a movement defined by means of manual input devices 7, 8. Control device 4 may also be set up in such a way that it regulates the movement of robotic arms 2, 3 and/or of the drives.

Robotic surgical system 1 is configured for use on a patient "P" lying on a surgical table "ST" to be treated in a minimally invasive manner by means of a surgical instrument, e.g., electromechanical instrument 10. Robotic surgical system 1 may also include more or less than two robotic arms 2, 3, the additional robotic arms likewise being connected to control device 4 and being telemanipulatable by means of operating console 5. A surgical instrument, for example, electromechanical instrument 10 (including the electromechanical end effector), may also be attached to the additional robotic arm.

Figure 2:
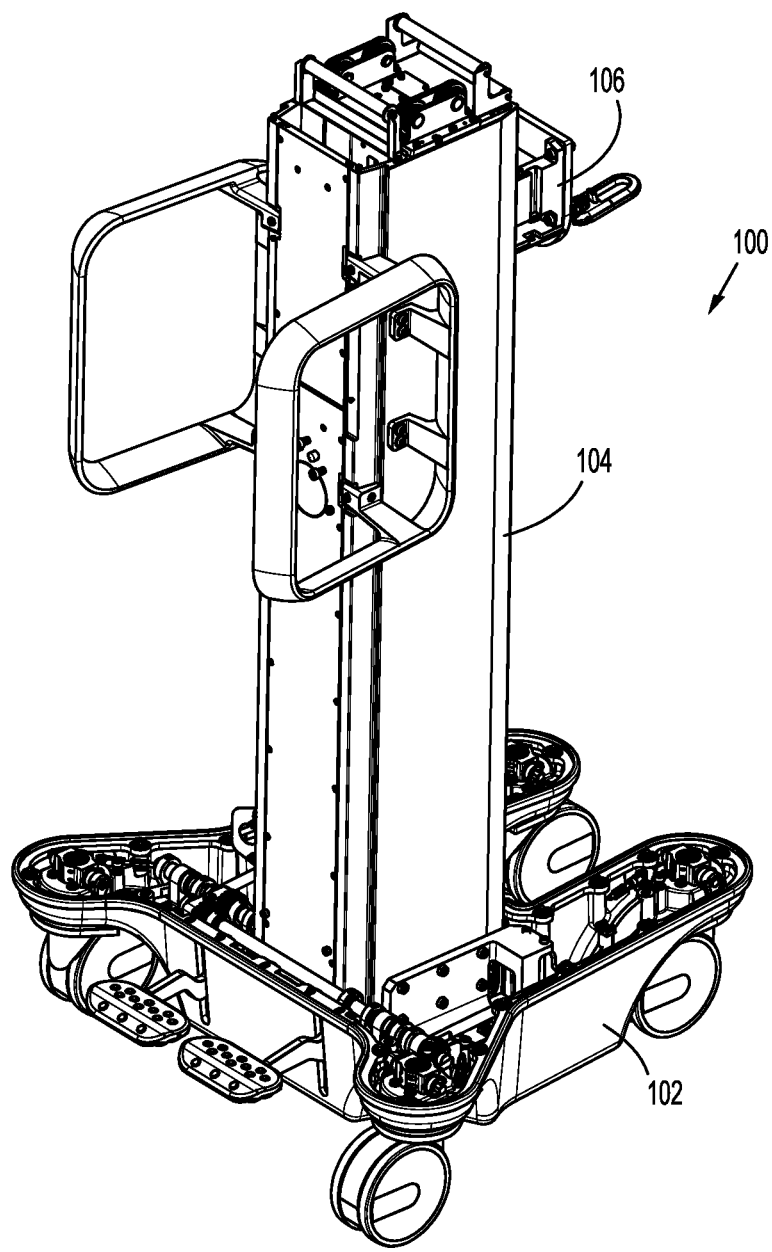
FIG. 2 is a perspective view of one embodiment of a surgical cart of the robotic surgical system of FIG. 1.

The robotic arms, such as for example, robotic arm 3, is supported on a surgical cart 100 (FIG. 2). The surgical cart 100 may incorporate the control device 4. In embodiments, the robotic arms, such as for example, robotic arm 2 may be coupled to the surgical table "ST."

For a detailed discussion of the construction and operation of a robotic surgical system, reference may be made to U.S. Pat. No. 8,828,023, entitled "Medical Workstation," the entire content of which is incorporated herein by reference.

With reference to FIG. 2, one exemplary embodiment of a surgical cart of robotic surgical system 1, configured for use in accordance with the present disclosure, is shown generally using reference numeral 100. The surgical cart 100 is configured to move robotic arm 3 (FIG. 1) to a selected position within operating room "OR" (FIG. 1) and to provide height adjustment of the robotic arm 3. The surgical cart 100 generally includes a cart base 102, a support column 104 extending vertically (i.e., perpendicularly) from the cart base 102, and a carriage or slider 106 slidably supported on the column 104 and configured for supporting the robotic arm 3 thereon.

With reference to FIGS. 2-5, the cart base 102 of the surgical cart 100 is fixed to a first end of the support column 104 and includes four casters 103a, 103b, 103c, 103d. In some embodiments, the cart base 102 may include more or less than four casters. The cart base 102 further includes two foot pedals 105a, 105b coupled to the casters 103a-103d via a braking mechanism 110 that functions to selectively unlock and lock the casters 103a-103d via actuation of the foot pedals 105a, 105b, respectively, as will be described in detail herein.

The braking mechanism 110 generally includes first and second rods 112, 114, first and second linkages 124, 134 coupled to the first rod 112, and first and second arms 148, 160 coupled to the second rod 114, each supported in the base 102. The first pedal 105a (e.g., a foot pedal) is non-rotationally coupled to the first rod 112, such that a depression of the first pedal 105a causes the first rod 112 to rotate in a first direction, indicated by arrow "A" in FIG. 5. The second pedal 105b (e.g., a foot pedal) is non-rotationally coupled to the second rod 114, such that a depression of the second pedal 105b causes the second rod 114 to likewise rotate in the first direction. The first and second rods 112, 114 are parallel to one another and are operably coupled to one another via corresponding couplers, such as, for example, spur gears 116, 118. In this way, the first and second rods 112, 114 rotate in opposite directions from one another. For example, if the first pedal 105a is depressed, the first rod 112 rotates in the first direction driving a rotation of the second rod 114 in a second, opposing direction, indicated by arrow "B" in FIG. 5.

Figure 3:
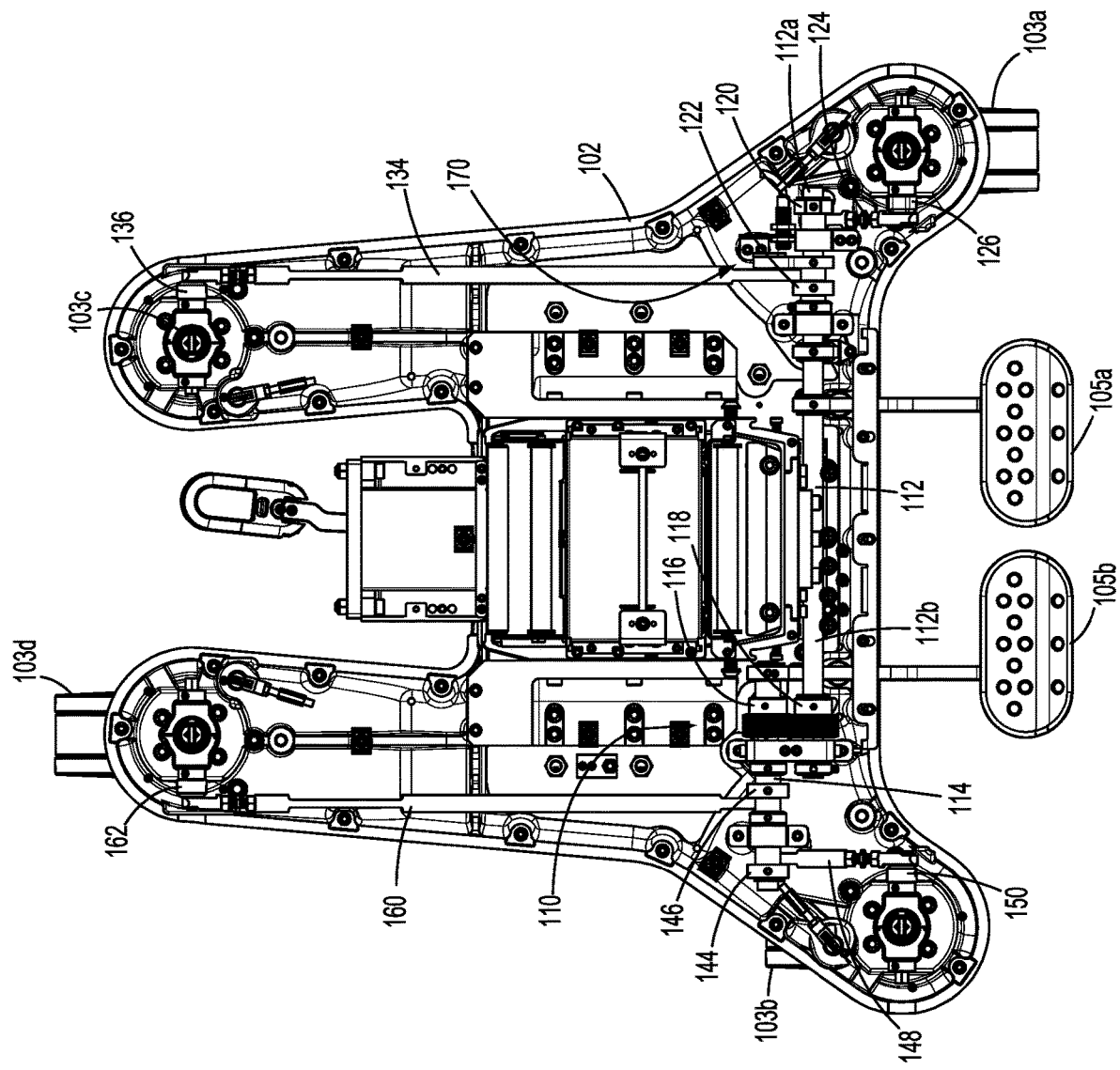
FIG. 3 is a top view, with a top cover removed, of the surgical cart of FIG. 2.
Figure 4:
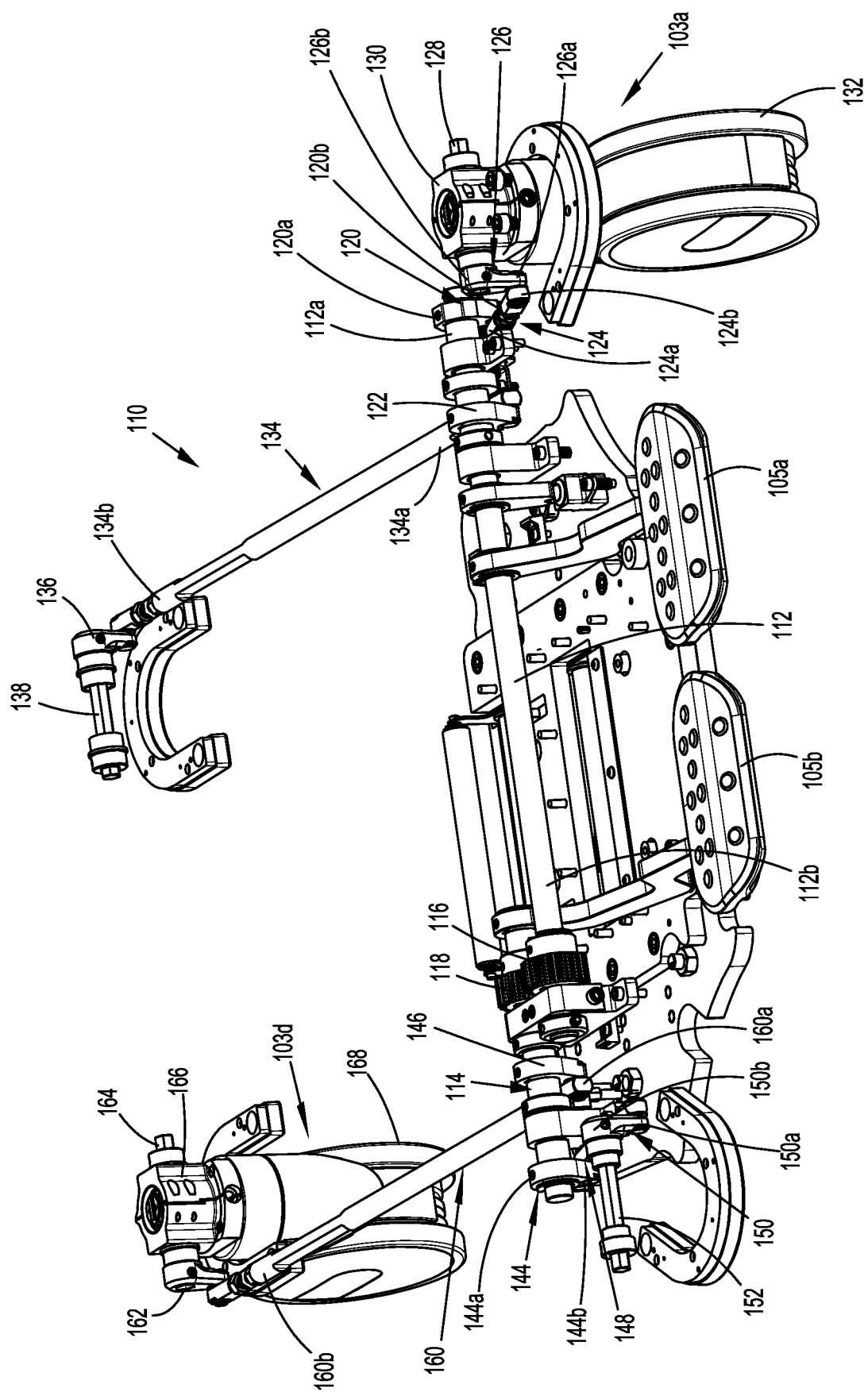
FIG. 4 is a rear, perspective view, with parts removed, of the surgical cart of FIG. 2.
Figure 5:
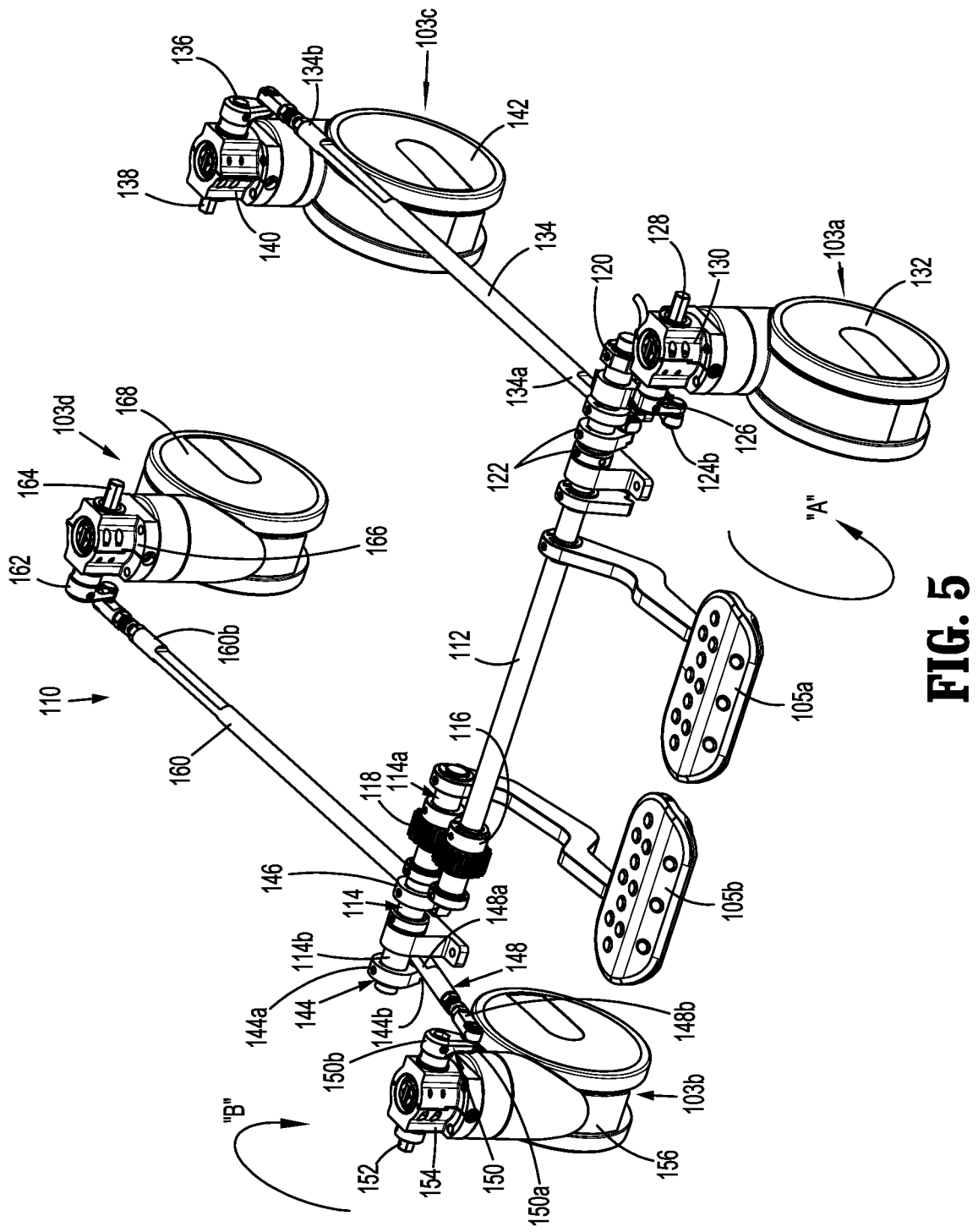
FIG. 5 is another rear, perspective view, with parts removed, of the surgical cart shown in FIG. 2.

With reference to FIGS. 3-5, the first rod 112 has a first end portion 112a and a second end portion 112b. The first end portion 112a of the first rod 112 has the gear 116 non-rotatably fixed thereto. The second end portion 112b of the first rod 112 is operably coupled to the first and third casters 103a, 103c. In particular, the second end portion 112b of the first rod 112 has a first crank 120 and a second crank 122 fixed thereto. The first crank 120 has a first end 120a non-rotationally coupled to the second end portion 112b of the first rod 112, such that the first crank 120 rotates with the first rod 112. The first crank 120 has a second end 120b having a first end portion 124a of the first linkage 124 rotationally coupled thereto.

The first linkage 124 of the braking mechanism 110 operably couples the first rod 112 to the first caster 103a. The first linkage 124 is perpendicular relative to the first rod 112 and may be shorter relative to the first rod 112. Since the first end portion 124a of the first linkage 124 is rotationally coupled to the second end 120b of the first crank 120, rotation of the first crank 120 with the first rod 112 drives a movement of the first linkage 124. The first linkage 124 has a second end portion 124b rotationally coupled to a crank 126 of the first caster 103c.

The crank 126 of the first caster 103a has a first end 126a rotationally coupled to the second end portion 124b of the first linkage 124, and a second end 126b non-rotationally coupled to a locking bar 128 of the first caster 103a. The locking bar 128 of the first caster 103a extends through a housing 130 of the first caster 103c and is configured to selectively lock and unlock a wheel 132 of the first caster 103a and lock and unlock a swiveling of the wheel 132 of the first caster 103c. It is contemplated that the locking bar 128 may have a non-circular transverse cross-sectional profile, such as hexagonal or any suitable polygon. The locking bar 128 may interact with a central locking mechanism or cam (not shown) inside of the caster 103a to unlock and lock the wheel 132.

In use, to unlock the first caster 103a, the first pedal 105a may be depressed to rotate the first rod 112 about its longitudinal axis in the direction indicated by arrow "A." Rotation of the first rod 112 in the first direction drives a rotation of the first crank 120 of the first rod 112, whereby the first crank 120 moves the first linkage 124 in a reciprocating/rotary type motion (e.g., translates and rotates) in a general direction toward the first rod 112 (i.e., away from the first caster 103a). Movement of the first linkage 124 towards the first rod 112 drives a rotation of the crank 126 of the first caster 103a and, in turn, the locking bar 128 of the first caster 103a in the first direction, to unlock the first caster 103a.

To lock the first caster 103a, the second pedal 105b may be depressed to rotate the second rod 114 about its longitudinal axis in the first direction indicated by arrow "A." Rotation of the second bar 114 in the first direction causes the first bar 112 to rotate in the opposing second direction indicated by arrow "B" due to the interaction of the gears 116, 118 of the corresponding first and second rods 112, 114. Rotation of the first rod 112 in the second direction drives a rotation of the first crank 120 of the first rod 112, whereby the first crank 120 moves the first linkage 124 in a general direction away from the first rod 112 in a reciprocating/rotary type motion. Movement of the first linkage 124 away from the first rod 112 drives a rotation of the crank 126 of the first caster 103a and, in turn, the locking bar 128 of the first caster 103a in the second direction, to lock the first caster 103a.

With continued reference to FIGS. 3-5, the second linkage 134 of the braking mechanism 110 operably couples the first rod 112 and the third caster 103c. More specifically, the second linkage 134 has a first end portion 134a rotationally coupled to the second crank 122 of the first rod 112, and a second end portion 134b rotationally coupled to a crank 136 of the third caster 103c. As such, rotation of the second crank 122 with the first rod 112 drives a reciprocating/rotary type movement of the second linkage 134. The second linkage 134, the second crank 122 of the first rod 122, and the crank 136 of the third caster 103c work together in a similar manner as the first linkage 124, the first crank 120 of the first rod 112, and the crank 126 of the first caster 103a described above.

The crank 136 of the third caster 103c is non-rotationally coupled to a locking bar 138 of the third caster 103c. The locking bar 138 of the third caster 103c extends through a housing 140 of the third caster 103c and is configured to selectively lock and unlock a wheel 142 of the third caster 103c and lock and unlock a swiveling of the wheel 142 of the third caster 103c.

In use, to unlock the third caster 103c, the first pedal 105a may be depressed to rotate the first rod 112 about its longitudinal axis in the direction indicated by arrow "A." Rotation of the first rod 112 in the first direction drives a rotation of the second crank 122 of the first rod 112, whereby the second crank 122 moves the second linkage 134 (e.g., translates and rotates) in a general direction away from the first rod 112. Movement of the second linkage 134 away from the first rod 112 drives a rotation of the crank 136 of the third caster 103c and, in turn, the locking bar 138 of the first caster 103c in a direction configured to unlock the third caster 103c.

To lock the third caster 103c, the second pedal 105b may be depressed to rotate the second rod 114 about its longitudinal axis in the first direction indicated by arrow "A." Rotation of the second rod 114 in the first direction causes the first rod 114 to rotate in the opposing second direction indicated by arrow "B" due to the interaction of the gears 116, 118 of the corresponding first and second rods 112, 114. Rotation of the first rod 112 in the second direction drives a rotation of the second crank 122 of the first rod 112, whereby the second crank 122 moves the second linkage 134 in a general direction toward the first rod 112. Movement of the second linkage toward the first rod 112 drives a rotation of the crank 136 of the third caster 103c and, in turn, the locking bar 138 of the third caster 103c in a direction configured to lock the third caster 103c.

With continued reference to FIGS. 2-5, the second rod 114 of the braking mechanism 110 has a first end portion 114a and a second end portion 114b. The first end portion 114a of the second rod 114 has the gear 118 non-rotatably fixed thereto. The second end portion 114b of the second rod 114 is operably coupled to the second and fourth casters 103b, 103d. In particular, the second end portion 114b of the second rod 114 has a first crank 144 and a second crank 146 fixed thereto. The first crank 144 of the second rod 114 has a first end 144a non-rotationally coupled to the second end portion 114b of the second rod 114, such that the first crank 144 rotates with the second rod 114. The first crank 144 has a second end 144b having a first end portion 148a of the first arm 148 rotationally coupled thereto.

The first arm 148 of the braking mechanism 110 operably couples the second rod 114 to the second caster 103b. The first arm 148 is perpendicular relative to the second rod 114 and may be shorter relative to the second rod 114. Since the first arm 148 is rotationally coupled to the first crank 144, rotation of the first crank 144 with the second rod 114 drives a movement of the first arm 148. The first arm 148 has a second end portion 148b rotationally coupled to a crank 150 of the second caster 103b.

The crank 150 of the second caster 103b has a first end 150a rotationally coupled to the second end portion 148b of the first arm 148, and a second end 150b non-rotationally coupled to a locking bar 152 of the second caster 103b. The locking bar 152 of the second caster 103b extends through a housing 154 of the second caster 103b and is configured to selectively lock and unlock a wheel 156 of the second caster 103b and lock and unlock a swiveling of the wheel 156 of the second caster 103b.

In use, to unlock the second caster 103b, the first pedal 105a may be depressed to rotate the first rod 112 about its longitudinal axis in the direction indicated by arrow "A." Rotation of the first rod 112 in the first direction drives a rotation of the second rod 114 in the opposing second direction, as indicated by arrow "B." The first crank 144 of the second rod 114 rotates with the second rod 114, whereby the first crank 144 moves the first arm 148 (e.g., translates and rotates) in a general direction away from the second rod 114. Movement of the first arm 148 away from the second rod 114 drives a rotation of the crank 150 of the second caster 103b and, in turn, the locking bar 152 of the second caster 103b in a direction configured to unlock the second caster 103b.

To lock the second caster 103b, the second pedal 105b may be depressed to rotate the second rod 114 about its longitudinal axis in the first direction indicated by arrow "A." Rotation of the second rod 114 in the first direction drives a rotation of the first crank 144 of the second rod 114, whereby the first crank 144 moves the first arm 148 in a general direction toward the second rod 114. Movement of the first arm 148 toward the second rod 114 drives a rotation of the crank 150 of the second caster 103b and, in turn, the locking bar 152 of the second caster 103b in a direction configured to lock the second caster 103b.

The second arm 160 of the braking mechanism 110 operably couples the second rod 114 and the fourth caster 103d. More specifically, the second arm 160 has a first end portion 160a rotationally coupled to the second crank 146 of the second rod 114, and a second end portion 160b rotationally coupled to a crank 162 of the fourth caster 103d. As such, rotation of the second crank 146 with the second rod 114 drives a movement of the second arm 160. The second arm 160, the second crank 146 of the second rod 114, and the crank 162 of the fourth caster 103d work together in a similar manner as the first arm 148, the first crank 144 of the second rod 114, and the crank 150 of the second caster 103b described above.

The crank 162 of the fourth caster 103d is non-rotationally coupled to a locking bar 164 of the fourth caster 103d. The locking bar 164 of the fourth caster 103d extends through a housing 166 of the fourth caster 103d and is configured to selectively lock and unlock a wheel 168 of the fourth caster 103d and lock and unlock a swiveling of the wheel 168 of the fourth caster 103d.

In use, to unlock the fourth caster 103d, the first pedal 105a may be depressed to rotate the first rod 112 about its longitudinal axis in the direction indicated by arrow "A." Rotation of the first rod 112 in the first direction drives a rotation of the second rod 114 in the opposing second direction, as indicated by arrow "B." The second crank 146 of the second rod 114 rotates with the second rod 114, whereby the second crank 146 moves the second arm 160 (e.g., translates and rotates) in a general direction toward the second rod 114. Movement of the second arm 160 toward the second rod 114 drives a rotation of the crank 162 of the fourth caster 103 and, in turn, the locking bar 164 of the fourth caster 103d in a direction configured to unlock the fourth caster 103d.

To lock the fourth caster 103d, the second pedal 105d may be depressed to rotate the second rod 114 about its longitudinal axis in the first direction indicated by arrow "A." Rotation of the second bar 114 in the first direction drives a rotation of the second crank 146 of the second rod 114, whereby the second crank 146 moves the second arm 160 in a general direction away from the second rod 114. Movement of the second arm 160 away from the second rod 114 drives a rotation of the crank 162 of the fourth caster 103d and, in turn, the locking bar 164 of the fourth caster 103d in a direction configured to lock the fourth caster 103d.

As can be appreciated from the above, the braking mechanism 110 provides for a simultaneous or near simultaneous unlocking of all the casters 103a-d via actuation of the first pedal 105a, and a simultaneous or near simultaneous locking of all the casters 103a-d via actuation of the second pedal 105b. In embodiments, the braking mechanism 110 may be configured so that a depression or lifting of the first pedal 105a may result in a locking or unlocking of the casters 103a-d, or a depression or lifting of the second pedal 105b may result in a locking or unlocking of the casters 103a-d.

Figure 6:
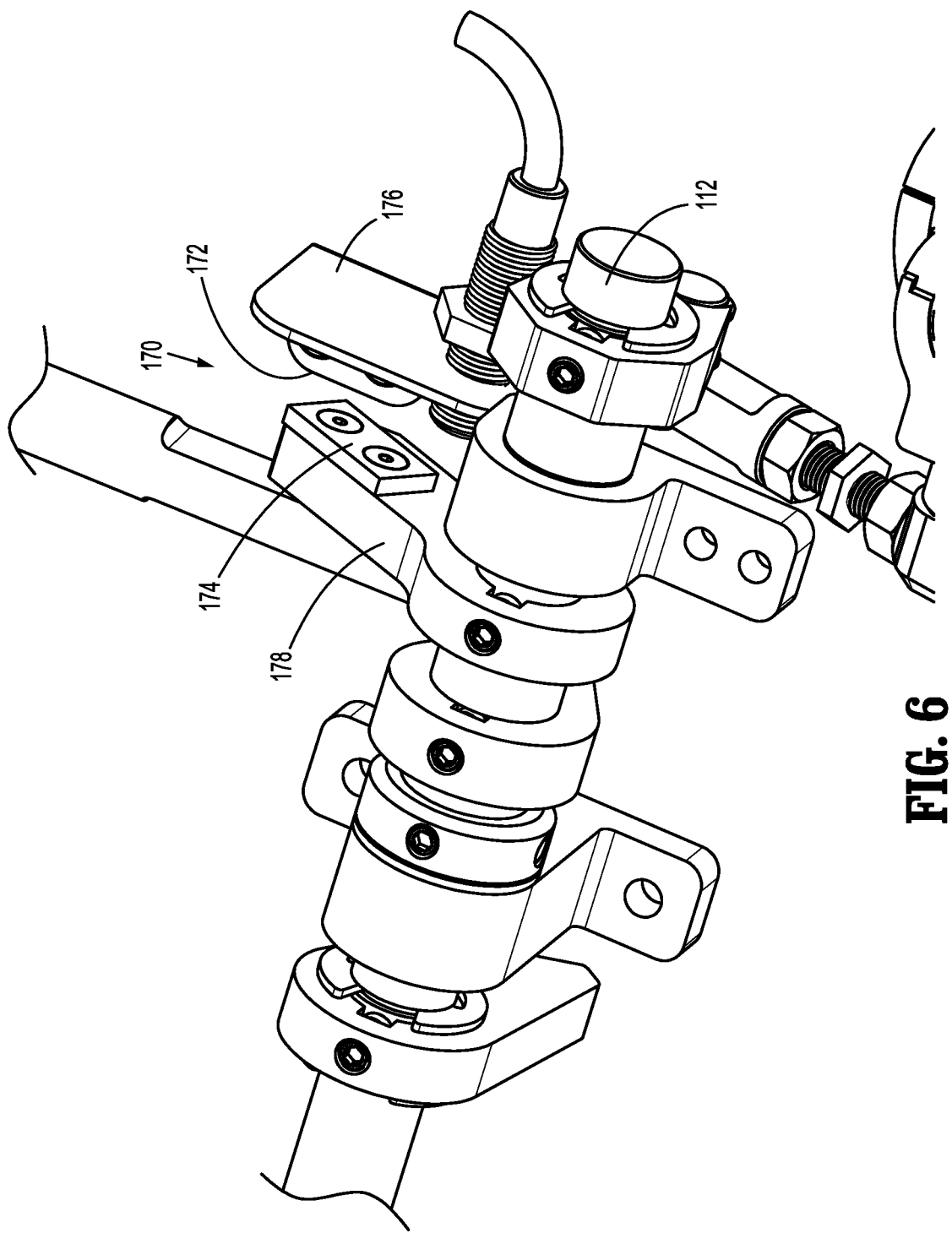
FIG. 6 is an enlarged view of a sensor assembly of the surgical cart of FIG. 2.

With reference to FIG. 6, the braking mechanism 110 may further include a sensing assembly 170 for determining whether the casters 103a-d are in a locked or an unlocked condition. The sensing assembly 170 includes a sensing element 172, such as, for example, a hall effect sensor, and a sensed element 174, such as, for example, a magnet. In embodiments, the sensing assembly 170 may include any suitable position sensors, such as, for example, a potentiometer, a proximity sensor, a rotary encoder, a linear variable differential transformer, an eddy-current sensor, or the like. The sensing element 172 is fixed to the base 102 (FIG. 3) of the cart 100 with a first flange 176, and the sensed element 174 is coupled to the first rod 112 with a second flange 178. The second flange 178 is non-rotationally coupled to the first rod 112, such that the second flange 178, along with the sensed element 174, rotates with the first rod 112. It is contemplated that the sensed element 174 may be attached to any suitable components of the braking mechanism 110, such as, for example, the second rod 114, the first or second linkages 124, 134, or the first or second arms 148, 160.

The sensed element 174 and the sensing element 172 are disposed adjacent one another and move in and out of alignment during a locking and unlocking of the braking mechanism 110. For example, in use, upon depressing the first pedal 105a (FIG. 3) to unlock the braking mechanism 110, the first rod 112 is rotated in the first direction, thereby rotating the second flange 178 of the sensing assembly 170 therewith. Rotation of the second flange 178 moves the sensed element 174 from a first position, in which the sensed element 174 is out of alignment with the sensing element 172, as shown in FIG. 6, to a second position, in which the sensed element 174 is aligned with the sensing element 172. When the sensed element 174 is in the second position, the sensing element 172 transmits a corresponding signal to the control device 4 (FIG. 1), which uses the signal to determine that the casters 103a-d are in an unlocked state. In embodiments, the cart 100 may be provided with an audio or visual indicator that the casters 103a-d are in an unlocked state.

Upon depressing the second pedal 105b to lock the braking mechanism 110, the second rod 114 is rotated in the first direction, which drives a rotation of the first rod 112 in the second direction, as described above. The second flange 178 of the sensing assembly 170 rotates with the second rod 114 in the second direction. Rotation of the second flange 178 moves the sensed element 174 relative to the sensing element 172 from the second position to the first position. When the sensed element 174 is in the first position, the sensing element 172 transmits a corresponding signal to the control device 4 (FIG. 1), which uses the signal to determine that the casters 103a-d are in a locked state.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the claimed invention. Therefore, the above description should not be construed as limiting, but merely as exemplifications of particular embodiments. Those skilled in the art will envision other modifications within the scope and spirit of the claims appended hereto.

What is claimed is:

1. A surgical cart for supporting a robotic arm, comprising:
    a base;
    a plurality of casters coupled to the base;
    a first rod rotatably supported by the base and operably coupled to a first caster of the plurality of casters, the first rod being configured to rotate in a first direction to one of lock or unlock the first caster; and
    a second rod rotatably supported by the base and operably coupled to a second caster of the plurality of casters, the second rod being operably coupled to the first rod such that rotation of the first rod in the first direction causes the second rod to rotate in a second direction to one of lock or unlock the second caster.

2. The surgical cart according to claim 1, wherein rotation of the second rod in the first direction is configured to cause the first rod to rotate in the second direction to the other of lock or unlock the first and second casters.

3. The surgical cart according to claim 1, wherein the first and second rods are parallel to one another.

4. The surgical cart according to claim 1, further comprising:
    a first pedal coupled to the first rod and configured to rotate the first rod in the first direction and in turn rotate the second rod in the second direction; and
    a second pedal coupled to the second rod and configured to rotate the second rod in the first direction and in turn rotate the first rod in the second direction.

5. The surgical cart according to claim 1, wherein rotation of the first rod in the first direction unlocks the first caster and rotation of the second rod in the second direction unlocks the second caster, and wherein rotation of the second rod in the first direction locks the second caster and rotation of the first rod in the second direction locks the first caster.

6. The surgical cart according to claim 1, further comprising a first linkage having a first end rotationally coupled to a first crank of the first rod, and a second end operably coupled to the first caster, wherein rotation of the first rod in the first direction moves the first linkage via the first crank to one of lock or unlock the first caster.

7. The surgical cart according to claim 6, wherein rotation of the first rod in the second direction moves the first linkage via the first crank to the other of lock or unlock the first caster.

8. The surgical cart according to claim 6, wherein the first linkage is perpendicular to the first and second rods.

9. The surgical cart according to claim 6, wherein the first caster has a crank operably coupled thereto, the second end of the first linkage being rotationally coupled to the crank of the first caster such that the movement of the first linkage rotates the crank of the first caster to one of lock or unlock the first caster.

10. The surgical cart according to claim 9, wherein the first caster has a locking bar non-rotationally coupled to the crank of the first caster, wherein rotation of the locking bar via the crank of the first caster one of locks or unlocks the first caster.

11. The surgical cart according to claim 6, further comprising a second linkage having a first end rotationally coupled to a second crank of the first rod, and a second end operably coupled to a third caster of the plurality of casters, wherein rotation of the first rod in the first direction moves the second linkage via the second crank to one of lock or unlock the third caster.

12. The surgical cart according to claim 11, wherein the first and second linkages are perpendicular to the first and second rods.

13. The surgical cart according to claim 11, wherein the third caster has a crank operably coupled thereto, the second end of the second linkage rotationally coupled to the crank of the third caster, such that the movement of the second linkage rotates the crank of the third caster to one of lock or unlock the third caster.

14. The surgical cart according to claim 13, wherein the third caster has a locking bar non-rotationally coupled to the crank of the third caster, such that rotation of the locking bar of the third caster via the crank of the third caster one of locks or unlocks the third caster.

15. The surgical cart according to claim 1, further comprising a first arm having a first end rotationally coupled to a first crank of the second rod, and a second end operably coupled to the second caster, wherein rotation of the second rod in the second direction moves the first arm via the first crank of the second rod to one of lock or unlock the second caster.

16. The surgical cart according to claim 15, wherein rotation of the second rod in the first direction moves the first arm via the first crank of the second rod to the other of lock or unlock the second caster.

17. The surgical cart according to claim 15, wherein the second caster has a crank operably coupled thereto, the second end of the first arm rotationally coupled to the crank of the second caster, such that the movement of the first arm rotates the crank of the second caster to one of lock or unlock the second caster.

18. The surgical cart according to claim 15, further comprising a second arm having a first end rotationally coupled to a second crank of the second rod, and a second end operably coupled to a fourth caster of the plurality of casters, wherein rotation of the second rod in the first direction moves the second arm via the second crank of the second rod to one of lock or unlock the fourth caster.

19. The surgical cart according to claim 1, wherein each of the first and second rods has a gear non-rotationally coupled thereto, the gears of the first and second rods interfacing with one another.

20. The surgical cart according to claim 1, wherein locking the first caster includes at least one of preventing rotation of a wheel of the first caster or preventing swiveling of the first caster.

\* \* \* \* \*